(12) United States Patent
Shankman (10) Patent No.: US 8,820,648 B2
(45) Date of Patent: Sep. 2, 2014

(54) PRECIOUS METAL AUTHENTICATION SYSTEM AND METHOD

(75) Inventor: Richard S. Shankman, Boca Raton, FL (US)

(73) Assignee: Peerless Worldwide, LLC, Boca Raton, FL (US)

( * ) Notice: Subject to any disclaimer, the term of this patent is extended or adjusted under 35 U.S.C. 154(b) by 0 days.

(21) Appl. No.: 14/008,485

(22) PCT Filed: Mar. 28, 2012

(86) PCT No.: PCT/US2012/030949
§ 371 (c)(1),
(2), (4) Date: Mar. 22, 2014

(87) PCT Pub. No.: WO2012/135346
PCT Pub. Date: Oct. 4, 2012

(65) Prior Publication Data
US 2014/0197242 A1    Jul. 17, 2014

Related U.S. Application Data

(60) Provisional application No. 61/468,245, filed on Mar. 28, 2011.

(51) Int. Cl.
*G06K 19/06* (2006.01)
*G07D 5/00* (2006.01)
*G06K 19/07* (2006.01)
*G06K 19/077* (2006.01)

(52) U.S. Cl.
CPC .......... *G06K 19/07749* (2013.01); *G07D 5/005* (2013.01); *G06K 19/0723* (2013.01)
USPC .......................................... 235/492; 235/494

(58) Field of Classification Search
CPC ................................................ G06K 19/00749
USPC .................................................. 235/492, 494
See application file for complete search history.

(56) References Cited

U.S. PATENT DOCUMENTS

| 8,750,570 B2 * | 6/2014 | Kerschner et al. ............ 382/103 |
| 2005/0072520 A1 * | 4/2005 | Berman ....................... 156/276 |

(Continued)

FOREIGN PATENT DOCUMENTS

| RU | 2174365 C1 | 10/2001 |
| RU | 2368294 C1 | 9/2009 |
| RU | 2380761 C2 | 1/2010 |

OTHER PUBLICATIONS

PCT International Search Report, PCT/US2012/030949, Form PCT/ISA/210, Jun. 18, 2012.
PCT Written Opinion of the International Searching Authority, PCT/US2012/030949, Form PCT/ISA/220, Jun. 18, 2012.

*Primary Examiner* — Christle I Marshall
(74) *Attorney, Agent, or Firm* — Nancy J. Flint, Esq.; Nancy J. Flint, Attorney At Law, P.A.

(57) ABSTRACT

Structures, systems, and methods verify the authenticity of a precious metal unit. A "ping bar" is designed to have a distinctive sound only if authentic and unadulterated. A "waffle bar" is shaped to discourage adulteration, damage, or counterfeiting and to facilitate easy core sampling and assay of the constituent metal's purity. Reeded edge features may additionally be employed to discourage tampering. An RFID device and a global registry system verify various attributes and ownership of the precious metal units.

3 Claims, 7 Drawing Sheets

(56) References Cited

U.S. PATENT DOCUMENTS

| | | |
|---|---|---|
| 2008/0149731 A1 | 6/2008 | Arai et al. |
| 2010/0313037 A1 | 12/2010 | Ward |
| 2011/0039042 A1* | 2/2011 | Johansen et al. ............... 428/29 |
| 2013/0062156 A1* | 3/2013 | Chandaria .................... 194/339 |
| 2014/0015643 A1* | 1/2014 | Shankman .................. 340/10.1 |

\* cited by examiner

PRECIOUS METAL AUTHENTICATION SYSTEM AND METHOD

BACKGROUND OF THE INVENTION

1. Field of the Invention

The invention pertains to the field of precious metal authenticity verification. More particularly, the invention pertains to structures, systems, and methods for verification of the purity, authenticity, and ownership tracking of precious metals.

2. Description of Related Art

Investment grade precious metal bars and rounds are produced in a variety of sizes, shapes, and purities. Precious metal rounds generally have a cylindrical or coin shape and are generally around 1 troy ounce in weight, although rounds in weights up to 100 kilograms have been produced. Precious metal bars are more commonly larger than rounds. Bars are generally commercially available in weights from about 1 troy ounce to over 1,000 troy ounces, in the case of Commodities Exchange (COMEX) "good delivery" ~400 oz. gold and ~1000 oz. silver bars. Precious metal bars and rounds are bought, sold, and traded daily by and between private individuals, retail dealers, wholesalers, and refiners.

The high value of precious metal, especially gold in even small amounts and silver bars of 100 troy ounces or more, makes them subject to theft, tampering, and outright counterfeiting. Conventional bars are typically formed en masse without any particular security features that can be used to identify a particular bar as belonging to a particular owner. Serial numbers appearing on some bars are seldom recorded for ownership identification purposes, and to date, there is no central global registry of ownership information to thwart theft. Conventional bars are also generally formed with substantially flat sides permitting core-drilling of the bars and insertion of inexpensive metal alloy slugs, creating "salted" or counterfeit bars of resulting substantially diminished value. These bars are then reintroduced into commerce to unsuspecting buyers.

Silver has a distinctive "ping" sound (resonance frequency) when struck. This is a longstanding and simplified technique used to tell if a silver bar is genuine or a lead, tungsten, or metal alloy counterfeit. The problem in the existing art is that there is no convenient way for a buyer or dealer to try to get a reliable and suitably repeatable (standardized), recognizable "ping" out of the multitude of forms that silver bars and rounds come in. Typically, another hard object, such as another bar or metal object, is used to strike the silver bar is or round being examined for authenticity to elicit the distinctive "ping". Even then, there is no standard resulting "ping" frequency to recognize, and producing a sufficient "ping" is not always easily accomplished due to the physical characteristics and various form configurations of the given bars or rounds.

It is these aforementioned deficiencies in the current state of the art that the present invention seeks to address and resolve.

SUMMARY OF THE INVENTION

Structures, systems, and methods verify the authenticity, origin of manufacture, purity, ownership, chain of custody, and status as stolen or not stolen of a precious metal unit. In one embodiment, the so-called "ping bar" is designed to exploit the distinctive resonant tone (a natural physics property) of a pure or near pure unit of silver in a method of authenticity verification. If tampered with, changes in the resonance upon percussion reveal the tampering to the prospective buyer or owner. In the case of smaller metal silver rounds, one embodiment contains certain surface shapes and structures designed to enhance the aforementioned natural resonant properties of the metal upon percussion.

In one embodiment, gold, platinum, palladium, and other precious metals comprise a so-called "waffle bar" designed to discourage any attempts at drilling, shaving, or otherwise altering the precious metals bar by employing a cast design that makes such attempts exceedingly difficult, if not impossible, and immediately obvious to the naked eye. In one embodiment, the IdentiGold™ system comprises a global registry system and/or an RFID chip device employed either individually or together, to verify the authenticity, ownership, chain of custody, and status (stolen or not stolen) of precious metal units.

DETAILED DESCRIPTION OF THE INVENTION

Precious metals, as used herein, are investment grade metals that are commonly bought, sold, or traded in the form of cast, extruded, or stamped bars and rounds, including, but not limited to, the metals gold, silver, platinum, and palladium.

A "precious metal unit," as used herein, is a unit of precious metal bullion formed in a predetermined shape and having a predetermined weight. Precious metal bullion is investment-grade precious metal that is used as an asset for monetary investment or trading purposes. Although precious metal units are conventionally formed as either bars or rounds, a precious metal unit may have any shape within the spirit of the present invention.

In one embodiment of the invention, an extruded, cast, or otherwise formed silver precious metal unit is shaped specifically to exhibit and possess various properties of a concussion idiophone, in that it is designed in such a way as to maximize the inherent resonance of the natural material, within certain commercially necessary or desirable functionality constraints and guidelines. In one embodiment, at least one surface of the silver precious metal unit comprises a flange defining an interior cavity. In one embodiment, the flange comprises a circle, an oval, a square, a rectangle or any other shape desired by the designer.

An idiophonic surface is disposed substantially at the base of the flange within the interior cavity which is designed to amplify the "ping" resonance frequency of the silver precious metal unit in a manner permitting a characteristic, repeatable, and recognizable tone. In one embodiment, the idiophonic surface comprises a concave surface. In one embodiment, the idiophonic surface comprises a convex surface.

In one embodiment, the idiophonic surface comprises one or more small protrusions or dimples designed to receive an impact and initiate a distinctive tone from the resonance "ping". In one embodiment, the idiophonic surface comprises a centrally located protrusion or dimple. In one embodiment, the idiophonic surface comprises a plurality of protrusions or dimples. The protrusions or dimples may be situated in a pattern, or may randomly be situated on the idiophonic surface.

In one embodiment, the walls of the flange comprise rounded "bubble"-type patterns, leading to a star-shaped idiophonic surface at the base of the flange, similar to the shapes employed in a steel drum instrument. Such "bubble-type" shapes are intended to accentuate the "ping" of a dropped coin or other sufficiently hard item (ball bearing, rock, etc.) hitting the base of the flange.

To prevent drilling or shaving of the edges of the silver precious metal unit, the casting may provide for distinctive reeded edge designs to prevent or discourage such attempts. Alternative physical form shapes of the silver precious metal unit, such as that of a tuning fork (designed to accentuate resonance), may be employed as well.

Figure 1A:
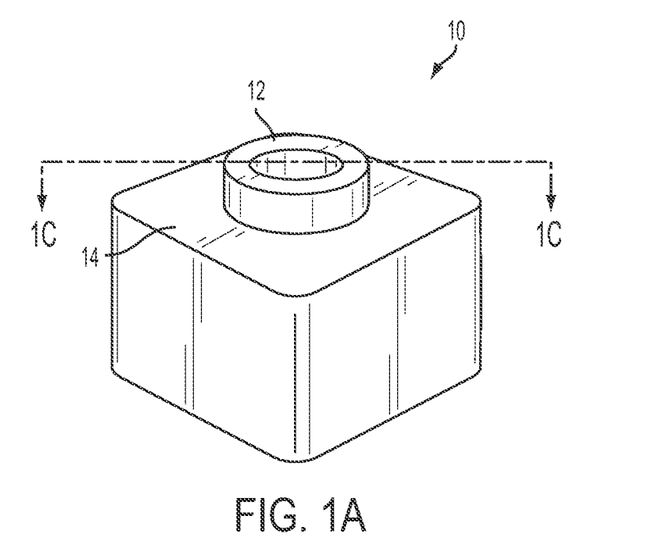
FIG. 1A shows a top view of a silver ping bar in one embodiment of the invention.
Figure 1B:
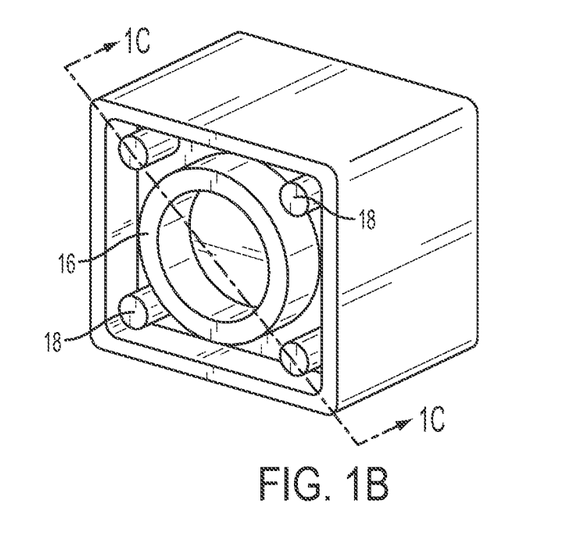
FIG. 1B shows a bottom view of the silver ping bar of FIG. 1A.
Figure 1C:
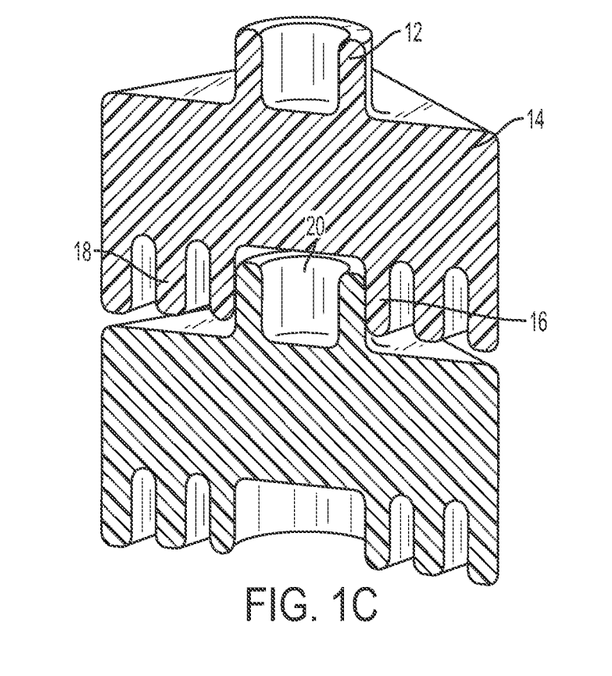
FIG. 1C shows a cross sectional side view of the ping bar of FIG. 1A along line 1C-1C in a stack with a second ping bar and a molded security insert between the two ping bars.

FIGS. 1A, 1B, and 1C depict a ping bar 10 according to one embodiment of the invention. Ping bar 10 comprises flange 12 extending from base 14 of ping bar 10. In one embodiment, base 14 and flange 12 are hollowed out through the back side and shaped to accentuate the ping sound (resonance) when ping bar 10 is struck. Back side of base 14 also includes receptacle 16 which can be designed to accommodate flange 12 to aid in stacking the silver precious metal units. Receptacle 16 may also accentuate the ping resonance frequency or produce a second resonance frequency different from the tone produced by striking flange 12. Back side of base 14 may also comprise a plurality of tuning rods 18, which may also act like tuning forks to produce a resonance frequency while also providing additional mass to ping bar 10. Base 14 may comprise a variety of thicknesses to provide more or less mass to ping bar 10. Ping bar 10 may have just one of resonance features 12, 16, 18 or any combination and arrangement of them. Resonance features 12, 16, and 18 are preferably arranged to allow stacking of multiple ping bars. Although base 14 is depicted as rectangular in FIGS. 1A and 1B, base 14 may alternatively be cylindrical or any other functional shape within the spirit of the invention.

In one embodiment of the invention, a verification system comprises an electronic security device or computer program configured to operate within an electronic device that recognizes the specific resonant ping tone made by an unadulterated precious metal unit.

FIG. 1C shows two ping bars 10 stacked with a storage and verification insert 20 that fits between the two ping bars 10 and prevents metal-to-metal contact between ping bars 10 in the stack. In one embodiment, the precious metal units are stackable by the use of an ancillary plastic insert that is substantially complementary in shape on opposite sides to the two units so that the insert fits between the two units to minimize space while preventing metal-to-metal contact and allowing stacking without scratching the units. The plastic insert may also serve as a security device by verifying the exact dimensions and security patterns of the shapes of the two units in that only unadulterated and genuine units fit into the shape and pattern of the insert.

Figure 2:
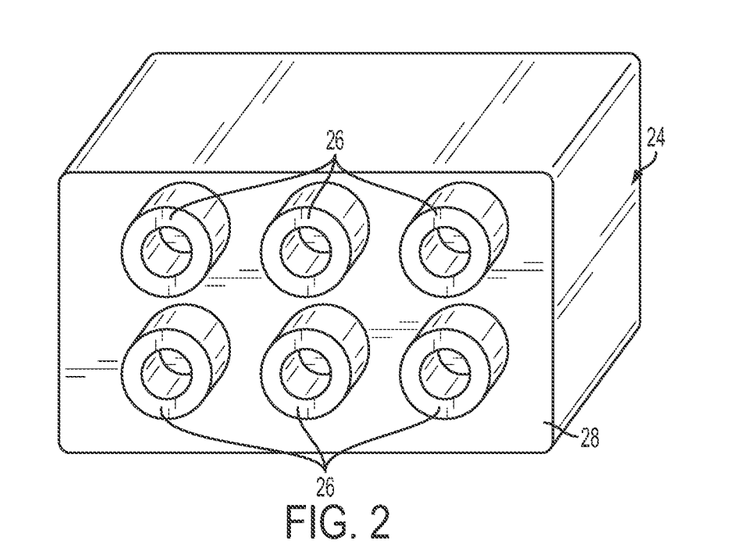
FIG. 2 shows a top view of a ping bar in one embodiment of the invention.

FIG. 2 depicts one embodiment of the invention comprising ping bar 24 with multiple flanges 26 and rectangular base 28. Flanges 26 may be identical in size or vary in size to produce a predetermined ping sound. Flanges 26 may be arranged in a regular array as shown in FIG. 2 or in an irregular predetermined arrangement to produce a predetermined ping sound.

Figure 3:
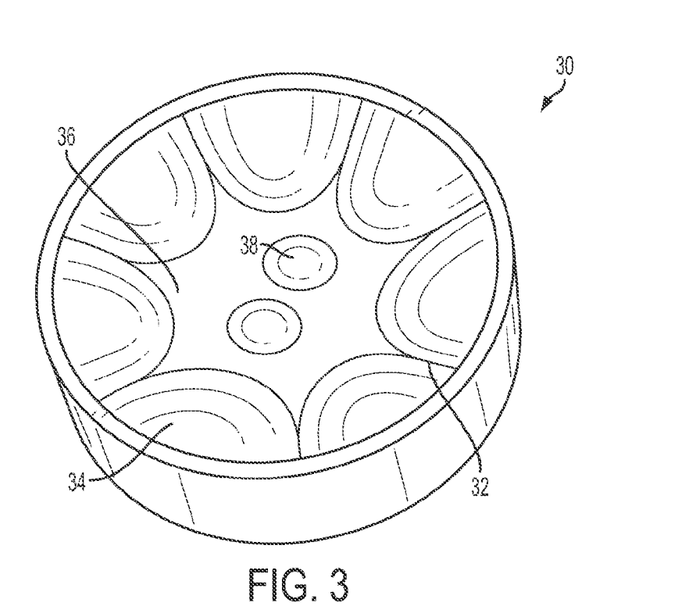
FIG. 3 shows an idiophonic ping bar in one embodiment of the invention.

FIG. 3 depicts a precious metal unit 30 comprising an idiophonic surface designed to amplify the "ping" resonance frequency in a manner permitting a characteristic, repeatable, and recognizable tone in the nature of a steelpan (also known as a steel drum). A tone is created in the idiophonic surface in the depicted embodiment with a star shape 32 that separates flat outer panels 34 from inner portion 36. Inner panel 36 may comprise a single flat panel or more than one flat panel 38.

Figure 4A:
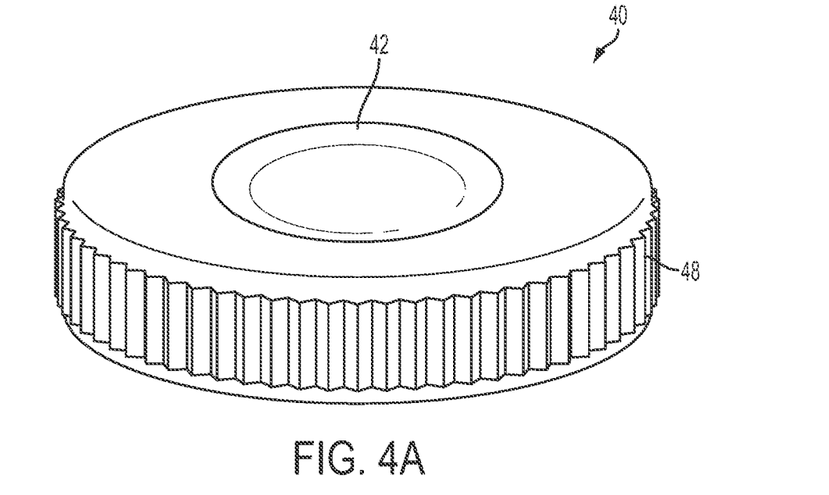
FIG. 4A shows a cross sectional side view of a "ping disk" in one embodiment of the invention.
Figure 4B:
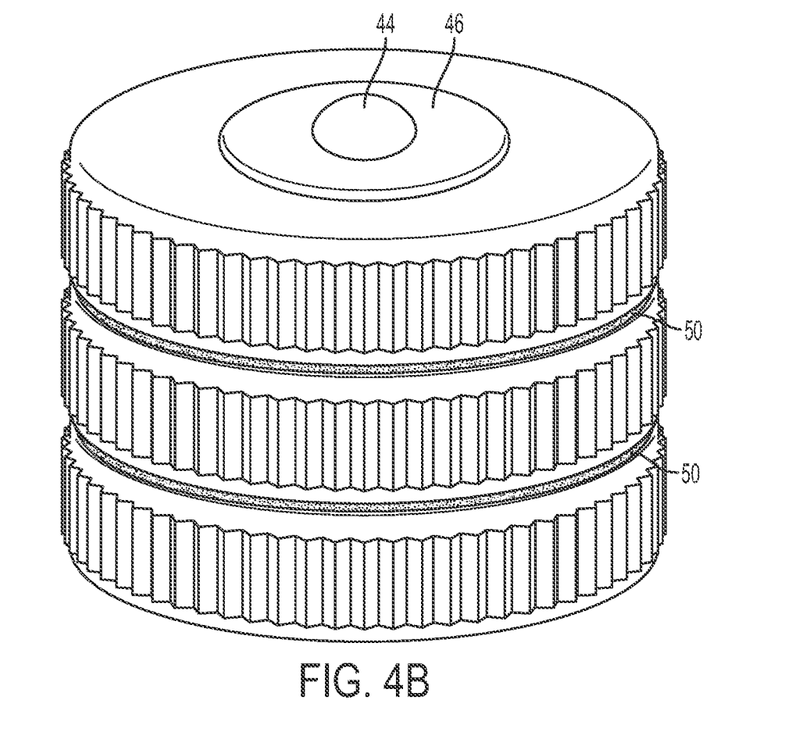
FIG. 4B shows a cross sectional side view of the ping disk of FIG. 4A in a stack with two other "ping disks" and molded security inserts between the ping disks.

FIG. 4A depicts a ping disk designed to make a characteristic, repeatable, and recognizable tone when dropped onto a solid surface. Ping disk 40 has a general flat cylindrical shape. One side of ping disk 40 comprises a concave curved shape 42 configured to project the resonance sound made from dropping ping disk 40 on a solid surface. The opposite side of ping disk 40 comprises a convex bump 44 extending from a raised portion 46. The outer circumference of ping disk 40 comprises a reeded edge 48 to discourage drilling. Ping disk 40 is designed to be dropped flat in the orientation shown in FIG. 4A onto a solid surface such that convex bump 44 strikes the solid surface first to produce the resonance sound of the ping disk. Raised portion 46 promotes stacking of multiple ping disks 40, as shown in FIG. 4B. A unique storage and verification insert 50 may also be used in stacking multiple ping disks.

Figure 5A:
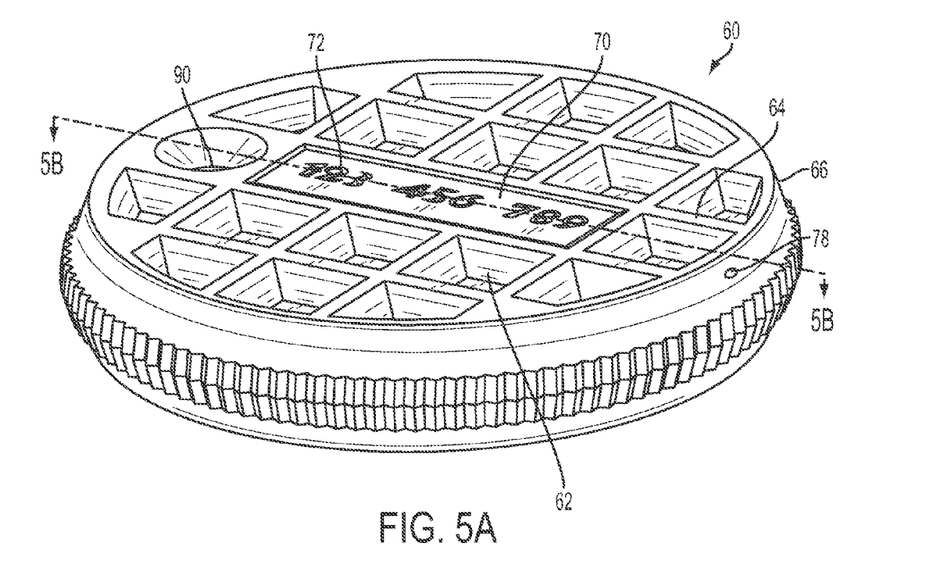
FIG. 5A shows a top view of a "waffle bar" in one embodiment of the invention.
Figure 5B:
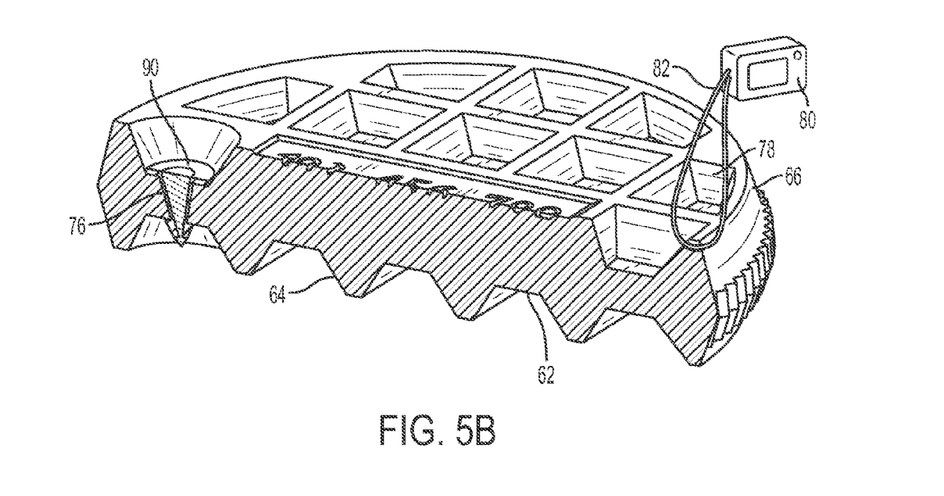
FIG. 5B shows a cross sectional side view of the waffle bar of FIG. 5A along line 5B-5B.

Other aspects of the invention relate to anti-counterfeiting techniques. In one embodiment, a precious metal unit is formed into the shape of a waffle bar. The flat top and bottom of the waffle bar are cast in a form resembling a typical waffle. The outer edges of the waffle bar may additionally be reeded or cast in waffle form to discourage tampering and adulteration. FIGS. 5A and 5B depict a waffle bar 60 that appears similar in pattern to a waffle on the top and bottom surfaces. Top and bottom surfaces of waffle bar 60 comprise numerous wells 62 in an array, separated by linear walls 64. Although waffle bar 60 in FIG. 5A is circular in shape, the general shape of waffle bar 60 may alternatively be square, rectangular or any other desired shape within the spirit of the invention.

Figure 6:
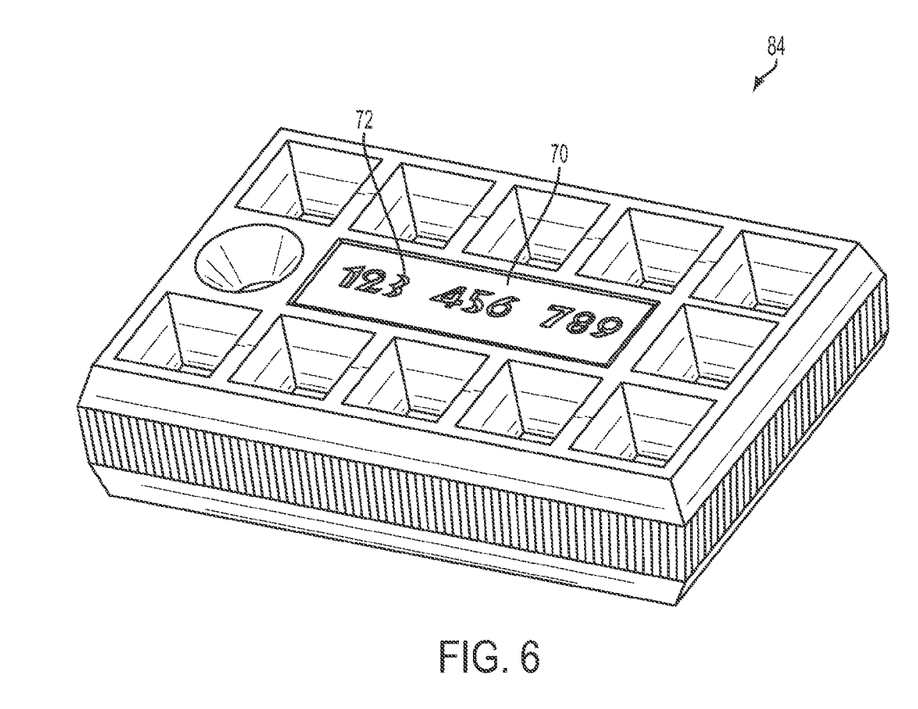
FIG. 6 shows a top view of a waffle bar in one embodiment of the invention.

FIG. 6 depicts a waffle bar 84 having a rectangular shape. Outer edge 66 may be reeded as shown in FIG. 5B to discourage drilling, shaving, or other adulteration to the outer edge 66 of waffle bar 84. One side of waffle bar 84 may comprise an engraving area 70 for indent or relief engraving of identifying indicia 72. A unique storage and verification insert (not shown) may also be used in stacking waffle bars 84.

Any attempt to drill, shave, or otherwise alter the waffle bar immediately results in noticeable deformation of the waffle pattern, revealing the attempt. There is likewise no way to employ a drill to remove a substantial enough portion of the waffle bar to facilitate economically-feasible counterfeiting. The only realistic method to employ to counterfeit a waffle bar would be to attempt to cast a replica (counterfeit) waffle bar made of an inexpensive metal alloy of similar weight and plate the surface in the subject precious metal. This resulting counterfeit waffle bar would, however, be easily detectable, as the waffle bar contains numerous thin-walled waffle pits that may be chosen at random for scratch-testing or drilling (with little or no cosmetic damage) to determine the metal composition of the interior of the bar. These waffle pits are designed to provide easy access into the center of the waffle bar itself, specifically facilitating easy authentication and assay of the bar's precious metal purity and authenticity.

In one embodiment of the anti-counterfeiting system and method of the invention, a radio-frequency identification (RFID) tag is associated with a particular precious metal unit. In one embodiment, the precious metal unit is formed in a shape to include a specific receptacle area and shape to permit the physical attachment of the RFID tag, including, but not limited to, a recess for insertion of the RFID tag or a through-hole. Various RFID tags are possible to accomplish this within the spirit of the invention. The RFID tags may be factory programmed and/or field programmed for use according to this embodiment of the invention.

The RFID tag and the precious metal unit are preferably formed such that the RFID tag is attachable to or integral with the precious metal unit, but the RFID tag is not removable without showing tamper evidence. In one embodiment, the RFID tag is similar to conventional livestock RFID ear tags with a tamper evidence system embedded in them. In one embodiment, the RFID tag has a corresponding hole and circular chamber in the precious metal unit to accommodate it. The RFID tag may have other identifying characteristic printed in its surface with a unique serial number printed around its circumference. In one embodiment, the RFID tag has a window in the center that is used as an anti-tamper evidence window. In one embodiment, a special device is required to apply the RFID tag to the precious metal unit. In one embodiment, the special device is an applicator gun, which may operate similarly to a common pop-rivet gun.

Figure 7A:
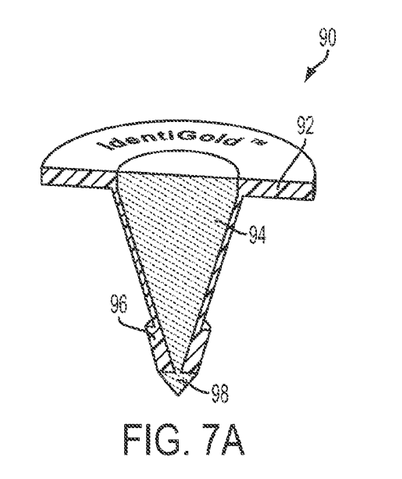
FIG. 7A shows a cross sectional side view of an RFID tag in one embodiment of the invention.
Figure 7B:
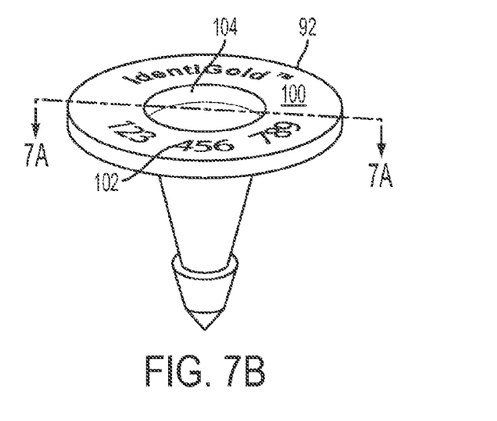
FIG. 7B shows a top view of the RFID tag of FIG. 7A, the cross sectional view of FIG. 7A being taken along line 7A-7A of FIG. 7B.
Figure 7C:
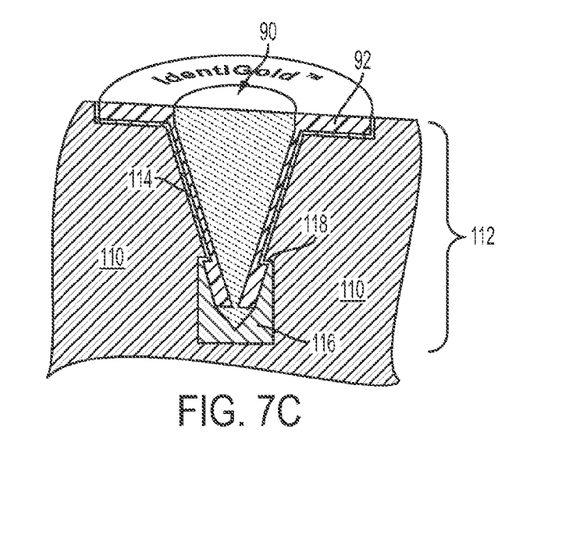
FIG. 7C shows a cross sectional side view of the RFID tag of FIG. 7A mounted in a precious metal unit.

The waffle bars 60 of FIG. 5A and FIG. 5B depict two methods of attaching RFID tags to precious metal units. In one embodiment, RFID tag 90, which is shown in more detail in FIGS. 7A through 7C, is disposed in a through-hole 76 in the middle of waffle bar 60. In one embodiment, through-hole 78 is disposed in outer edge 66 of waffle bar 60, which also receives cable 82 attached to RFID tag 80. Cable 82 may comprise a small diameter steel cable which serves as an electrical wire such that RFID tag 80 may record the instance of tampering if cable 82 is cut. Through-hole 76 and through-hole 78 may be reinforced with a dissimilar metal harder than precious metal unit if desired.

FIGS. 7A and 7B show RFID tag 90 for a precious metal unit. RFID tag 90 may be used with a precious metal unit of any general shape, including, but not limited to, a ping bar, a waffle bar, or any other conventional bar or a round. RFID tag 90 comprises a flat cylindrical upper portion 92 and a shaft 94 generally tapering down from upper portion 92 to a tip 98, with a ledge 96 formed on shaft 94 at about two-thirds of the distance down from flat cylindrical upper portion 92 to tip 98. As shown in FIG. 7B, upper portion 92 comprises an outer region 100 which may include useful identifying markings 102 and a cavity 104 which extends from upper portion 92 to tip 98. Cavity 104 may house the RFID tag 90 and may include an anti-tamper window feature (not shown).

FIG. 7C shows RFID tag 90 inserted into recess 112 in precious metal unit 110. Recess 112 comprises shaft 114 opening to larger chamber 116 so that complementary ledge 118 is formed in recess 112. RFID tag 90 is manufactured from a deformable material having sufficient flexibility such that ledge 96 compresses upon insertion of shaft 94 into recess 112 until shaft 94 allowing ledge 96 to enter and reside in chamber 116. Once shaft 94 and ledge 96 enter chamber 116, RFID tag 90 returns to its original shape such that complementary ledge 118 prevents ledge 16 and therefore shaft 94 from being withdrawn from precious metal unit 110 through recess 112. In one embodiment, recess 112 comprises a lining (not shown) that is manufactured from a deformable material having sufficient flexibility such that the lining compresses upon insertion of ledge 96 and shaft 94. In one embodiment, recess 112 comprises a through-hole (not shown). Although upper portion 92 of RFID tag 90 is shown as being located above the outer surface of precious metal unit 110 in FIG. 7A, in one embodiment recess 112 may include a complementary recess for receiving upper portion 92 such that the top surface of upper portion 92 is substantially level with or recessed below the neighboring outer surface of precious metal unit 110 as a further deterrent against tampering.

In one embodiment, the RFID tag comprises a thermally-protective coating and is inserted into the molten precious metal unit at the time of manufacture of the precious metal unit. Suitable thermally-protective coatings are more fully described in PCT Patent Application Serial No. PCT/US12/29693, filed on Mar. 19, 2012 and titled Thermally-Armored Radio-Frequency Identification Device and Method of Producing Same, the contents of which are hereby incorporated by reference in their entirety. The outer protective thermal armor may be any thermally-protective coating sufficient to protect the RFID tag from thermal damage, including, but not limited to:

(1) a modified polyphenylene ether (PPE)/olefin resin blend, including, but not limited to:
  (a) a Noryl® resin (GE Advanced Materials, Wilton, Conn., United States),
  (b) a polyphenylene oxide (PPO)/polystyrene (PS) alloy resin, including, but not limited to, a Noryl® PKN resin (GE Advanced Materials, Wilton, Conn., United States), and
  (c) a polyphenylene ether (PPO)/polypropylene (PP) alloy resin, including, but not limited to, a Noryl® PPX 615 alloy of polyphenylene ether (PPE) and polypropylene (PP) resin (GE Advanced Materials, Wilton, Conn., United States),
(2) a vinyl ester resin, including but not limited to, aromatic ethers and oligoethers with vinyl aromatic and methacrylate end groups capable of crosslinking and polycyclization, including, but not limited to:
  (a) a Rolivsan (RR) (Russian Academy of Sciences, Moscow, Russia) resin, and
  (b) a Zaitform (ZR) (Russian Academy of Sciences, Moscow, Russia) resin,
(3) a reinforced carbon-carbon (RCC) resin, including, but not limited to, a composite material of carbon fiber reinforcement in a graphite matrix,
(4) a phenolic resin,
(5) a ceramic enamel,
(6) a glass enamel,
(7) a vermiculite enamel,
(8) a silicate-based fiber or cloth resin-impregnated enamel, including, but not limited to, an asbestos-based fiber or cloth resin-impregnated enamel, (9) a flame-resistant meta-aramid material-based fiber or cloth resin-impregnated enamel, including, but not limited to, a Nomex® (E.I. du Pont de Nemours and Co., Wilmington, Del., United States)-based fiber or cloth resin-impregnated enamel, (10) a silicon-based resin, including, but not limited to, a silicon carbide epoxy resin, including, but not limited to:
  (a) a silicon carbide epoxy resin densified with tetraethyl orthosilicate (TEOS), and
  (b) an amorphous silica fiber resin with a colloidal silica binder, which may be sintered into the outer metal casing of the RFID chip,
  (c) an MA-25 Thermal Protection System (TPS) repair resin (Lockheed Martin Space Systems Co., New Orleans, La., United States).

(11) silica glass fibers, including, but not limited to, LI-900 (Lockheed Missiles and Space Company, Sunnyvale, Calif., United States), a matrix of 99.9% pure silica glass fibers with 94% by volume air for an overall density of 9 lb/ft$^3$, which is used on Space Shuttle thermal tiles, and (12) a multi-layer or multi-component composite coating including at least one of the above-mentioned coatings.

The material used for and the thickness of the thermal coating of the thermally-armored RFID tag are typically selected based on the maximum temperature to which the RFID tag is to be exposed during the manufacture of the precious metal unit. In one embodiment, the thermally-coated RFID tag comprises any thermally-protective coating, now known or later developed, sufficient to protect the RFID tag from thermal damage. In one embodiment, the thermal coating completely encapsulates the thermally-armored RFID tag. A person of ordinary skill in the art can coat the RFID tag according to the invention without undue experimentation The material used for and the thickness of the thermal coating are preferably selected based on the maximum temperature to which the RFID tag is to be exposed during the manufacture of the precious metal unit. The thermal coating employed preferably completely encapsulates the RFID tag concealed within the precious metal unit. In one embodiment, such as when the item to be tagged is a silver item, the thermal coating is effective to protect the RFID tag up to temperatures of at least 900° C. (1,652° F.). In one embodiment, such as when the item to be tagged is a pure silver item, the thermal coating is effective to protect the RFID tag up to temperatures of at least 1,000° C. (1,832° F.). In one embodiment, such as when the item to be tagged is a gold item, the thermal coating is effective to protect the RFID tag up to temperatures of at least 1,100° C. (2,012° F.). In one embodiment, such as when the item to be tagged is a palladium item, the thermal coating is effective to protect the RFID tag up to temperatures of at least 1,555° C. (2,831° F.). In one embodiment, such as when the item to be tagged is a platinum item, the thermal coating is effective to protect the RFID tag up to temperatures of at least 1,770° C. (3,220° F.).

Where the RFID tag is inserted into the molten precious metal at the time of forming the precious metal unit, the RFID tag is specially designed to transmit a radio frequency signal through the encapsulating precious metal unit. In one embodiment, the RFID tag and precious metal unit are designed such that the precious metal unit itself serves as an amplifying antenna for the RFID signal.

In one embodiment, the precious metal unit is encased in a security slab associated with an RFID tag. At least a portion of the security slab is preferably transparent such that the precious metal unit is visible through the security slab. In one embodiment, the transparent portion is made of a plastic or polymer. In one embodiment, a portion of the security slab is opaque. The opaque portion may be made of any opaque material, including, but not limited to, paper, cardboard, a plastic, or a metal. The RFID tag may be embedded in the security slab when the security slab is formed, or the RFID tag may be attached to the slab such as in the manners described above for attaching an RFID tag to the precious metal unit itself. Where the RFID tag is embedded in the security slab during formation of the security slab, the RFID tag may include a thermally-protective coating to protect it from the elevated temperatures of the security slab in a molten state. The security slab is preferably formed with at least one security features such that any attempt to remove or separate the precious metal unit or the RFID tag from the security slab is recorded or visually apparent.

Figure 8:
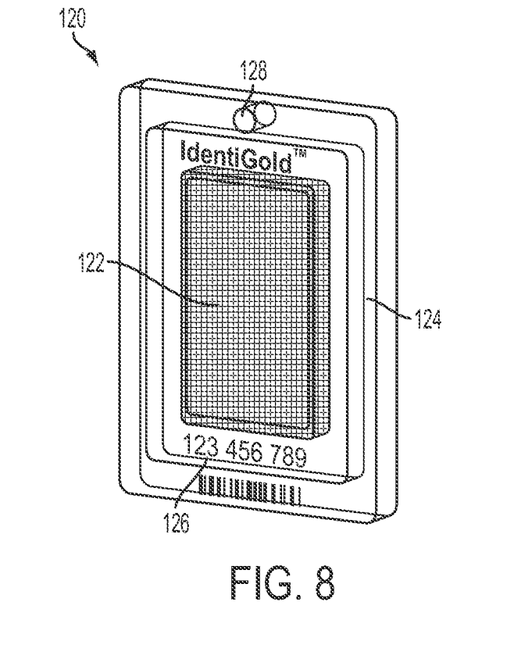
FIG. 8 shows an encased precious metal unit with an RFID tag in one embodiment of the invention.

FIG. 8 depicts encased and RFID-tagged precious metal unit 120, where precious metal unit 122 is encased in a transparent security slab 124. Indicia 126 on security slab 124 and RFID tag 128 embedded in security slab 124 provide for unique identification and authentication of precious metal unit 122.

Figure 9:
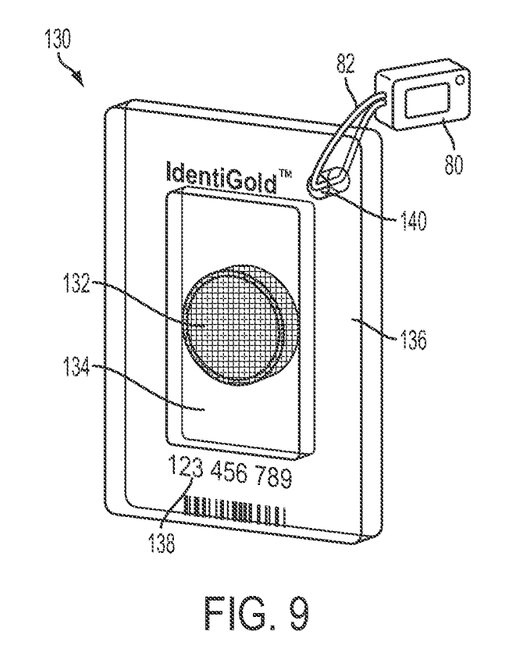
FIG. 9 shows an encased precious metal unit with an RFID tag in one embodiment of the invention.

FIG. 9 depicts encased and RFID-tagged precious metal unit 130, where the precious metal unit 132 is encased in a security slab that comprises transparent portion 134 and opaque portion 136. In this embodiment, security slab includes through-hole 140, which receives cable 82 of RFID tag 80. Cable 82 may comprise a small diameter steel cable which serves as an electrical wire such that RFID tag 80 may record the instance of tampering if cable 82 is cut. Indicia 138 and RFID tag 80 provide for the unique identification and authentication of precious metal unit 132.

In one embodiment of the anti-counterfeiting, tracking and registration system and method of the invention, an RFID tag associated with a precious metal unit is registered with a precious metals global registry system, such as the IdentiGold™ system, for registration, authentication, ownership, manufacturer identity, tracking, item purity (or fineness), "chain of custody", or theft status of the precious metal unit.

In one embodiment, the precious metals global registry system comprises a master website hosted on one or more servers. The master website further comprises one or more databases, a programmable processor and a communications link to a communications network. The master website is accessible over the communications network to a plurality of users which could include precious metals dealers, jewelry stores, foundries, retailers, coin shops and law enforcement or other governmental authorities. Databases are configured to store information relating to each RFID tag, including the unique RFID tag serial number, the location and production date of the precious metal unit associated with the RFID tag, the unique serial number of the precious metals unit, ownership information of the precious metal unit, information on purchase of the precious metal unit such as date and price, chain of title and chain of custody of the precious metal unit, purity information, information to validate the owner of the precious metal unit and any other information desired to be stored in relationship to an RFID tag. The programmable processor of the master website can be configured to access information in database in response to user inputs.

The precious metals global registry system can be used by any user who can access the master website over any known or later developed communications network by any suitable device now known or later developed. Where the precious metals global registry system is web-based, suitable devices include, but are not limited to, general purpose computers; laptop computers; thin clients; PDAs; cell phones; satellite phones; and smartphones. The device must be capable of rendering and displaying pages created by any markup language now known or later developed which are transmitted over the communications network by the master website by any web browser program now known or later developed. Suitable markup languages include, but are not limited to, HTML and XHTML. Suitable web browser programs include, but are not limited to, Google Chrome, Internet Explorer™, and Mozilla Firefox™.

The master website comprises a plurality of web pages hosted on one or more servers accessed over the communications network by way of a locator address, such as a URL or URI. The one or more servers include or are in communication with a central processing unit ("CPU"), or processor; a communications link to the communications network; and one or more searchable databases.

A user who wishes to access information on the precious metals global registry system accesses the master website through a web-enabled device. After entering the URL of the master website into the web browser program of the device, a communications link is established between the user's device (the "client") and the master website server (the "server"). The user's device may access the master website over any wired or wireless network now known or later developed, for example via a WAN, LAN, MAN, Bluetooth, Ethernet, Wi-Fi, satellite, GSM or PCS.

Once on the master website, the user is presented with a web page transmitted from the master website and rendered on the user's device that provides a number of options. The user enters the RFID tag serial number or the unique precious metals unit serial number, which is transmitted to the master website. In one embodiment, the RFID tag serial number or the unique precious metals unit serial number is detected using a reader or other interrogator and transmitted to the master website. The master website searches for file information associated with the RFID tag serial number or unique precious metals unit serial number and transmits at least part of that information to the user who transmitted the RFID tag serial number.

Stored information can include the status of the precious metals unit, such as theft, adulteration or counterfeiting. Receipt of information indicating any of these statuses can be transmitted to the user and/or to law enforcement for interception and seizure of the precious metals unit.

Information can be updated in the master website databases, such as ownership changes, however security measures can be employed to maintain confidentiality and security of the information. Information in the databases can be encrypted for additional confidentiality and security.

In one embodiment, the precious metals global registry system can be accessed over other communications systems, such as the POTS (Plain Old Telephone System). The user can communicate with the system via a live operator or via Computer Telephony/Voice Response Units.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A precious metal bullion object having anti-counterfeiting features, comprising:
a precious metal bullion object comprising one or more anti-counterfeiting features configured to evidence attempts to tamper with, remove or alter one or more of the anti-counterfeiting features, wherein the precious metal bullion object comprises a radio-frequency identification (RFID) tag,
wherein the RFID tag comprises a thermally-protective coating, wherein further the thermally-protective coated RFID tag is inserted into the molten precious metal object at the time of manufacture of the molten precious metal object.

2. The precious metal bullion object of claim 1, wherein the thermally-protective coating comprises a modified polyphenylene ether (PPE)/olefin resin blend, a vinyl ester resin, a reinforced carbon-carbon (RCC) resin, a phenolic resin, a ceramic enamel, a glass enamel, a vermiculite enamel, a silicate-based fiber, a cloth resin-impregnated enamel, a flame-resistant meta-aramid material-based fiber, a flame-resistant meta-aramid material-based cloth resin-impregnated enamel, a silicon-based resin, silica glass fibers, or a multi-layer or multi-component composite coating including at least one of the above-mentioned coatings.

3. The precious metal bullion object of claim 2, wherein the thermally-protective coating is effective to protect the RFID tag up to temperatures from about 900° C. (1,652° F.) to about 1,770° C. (3,220° F.).

* * * * *